United States Patent [19]

Uchida et al.

[11] Patent Number: 4,545,251
[45] Date of Patent: Oct. 8, 1985

[54] ELECTRONIC SCANNING TYPE ULTRASONIC NON-DESTRUCTIVE TESTING APPARATUS

[75] Inventors: Kuniharu Uchida, Fujisawa; Satoshi Nagai; Ichiroh Komura, both of Yokohama, all of Japan

[73] Assignee: Tokyo Shibaura Denki Kabushiki Kaisha, Kawasaki, Japan

[21] Appl. No.: 511,938

[22] Filed: Jul. 8, 1983

[30] Foreign Application Priority Data

Jul. 8, 1982 [JP] Japan ................... 57-118907

[51] Int. Cl.⁴ ................................. G01N 29/04
[52] U.S. Cl. .......................... 73/631; 73/1 DV; 73/628; 73/900
[58] Field of Search ............ 73/626, 628, 631, 900, 73/1 DV

[56] References Cited

U.S. PATENT DOCUMENTS

| | | | |
|---|---|---|---|
| 4,228,688 | 10/1980 | Sharpe | 73/631 |
| 4,248,091 | 2/1981 | Hashiguchi | 73/631 |
| 4,356,731 | 11/1982 | Mahony | 73/631 |
| 4,398,423 | 8/1983 | Takahashi | 73/631 |
| 4,442,713 | 4/1984 | Wilson et al. | 73/626 |
| 4,462,082 | 7/1984 | Thiele et al. | 73/631 |

OTHER PUBLICATIONS

Suta,S Catalogue by Southwest Research Institute, USA issued about 1978.

*Primary Examiner*—Howard A. Birmiel
*Attorney, Agent, or Firm*—Oblon, Fisher, Spivak, McClelland & Maier

[57] ABSTRACT

An ultrasonic non-destructive testing apparatus of the electronic scanning type comprising transmitter for producing exciting pulses in response to a predetermined timing pulse, a probe coupled to said transmitter, having a plurality of transducers for transmitting ultrasonic waves into a body to be tested and for receiving ultrasonic echo waves, signal processor coupled to said probe for processing said ultrasonic echo waves received by said probe to generate an echo wave signal, a memory coupled to said signal processor for storing reference data on an amplitude attenuation of an ultrasonic echo coming through each beam propagating path which is obtained by transmitting the ultrasonic waves into a calibration body at the time of a calibration, calculator coupled to said memory for calculating a predetermined correction value on the basis of said reference data stored in said memory, said predetermined correction value being at each crossing points on a two dimensional coordinate by applying a linear interpolation, correcting circuit coupled to said signal processor for correcting an amplitude attenuation of said echo wave signal by using said predetermined correction value at each crossing points to generate a corrected echo wave signal, and display device coupled to said correcting circuit for displaying a wave with regard to said body on the basis of the corrected echo wave signal.

14 Claims, 27 Drawing Figures

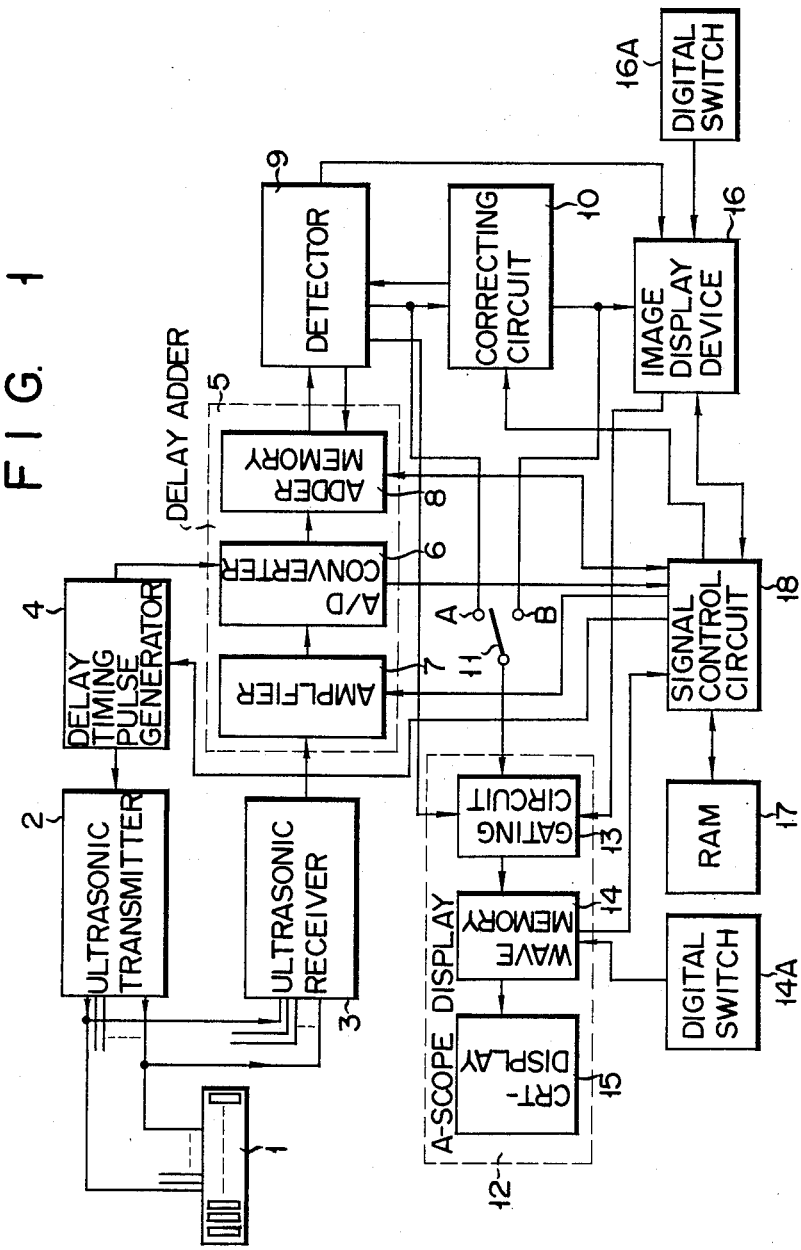

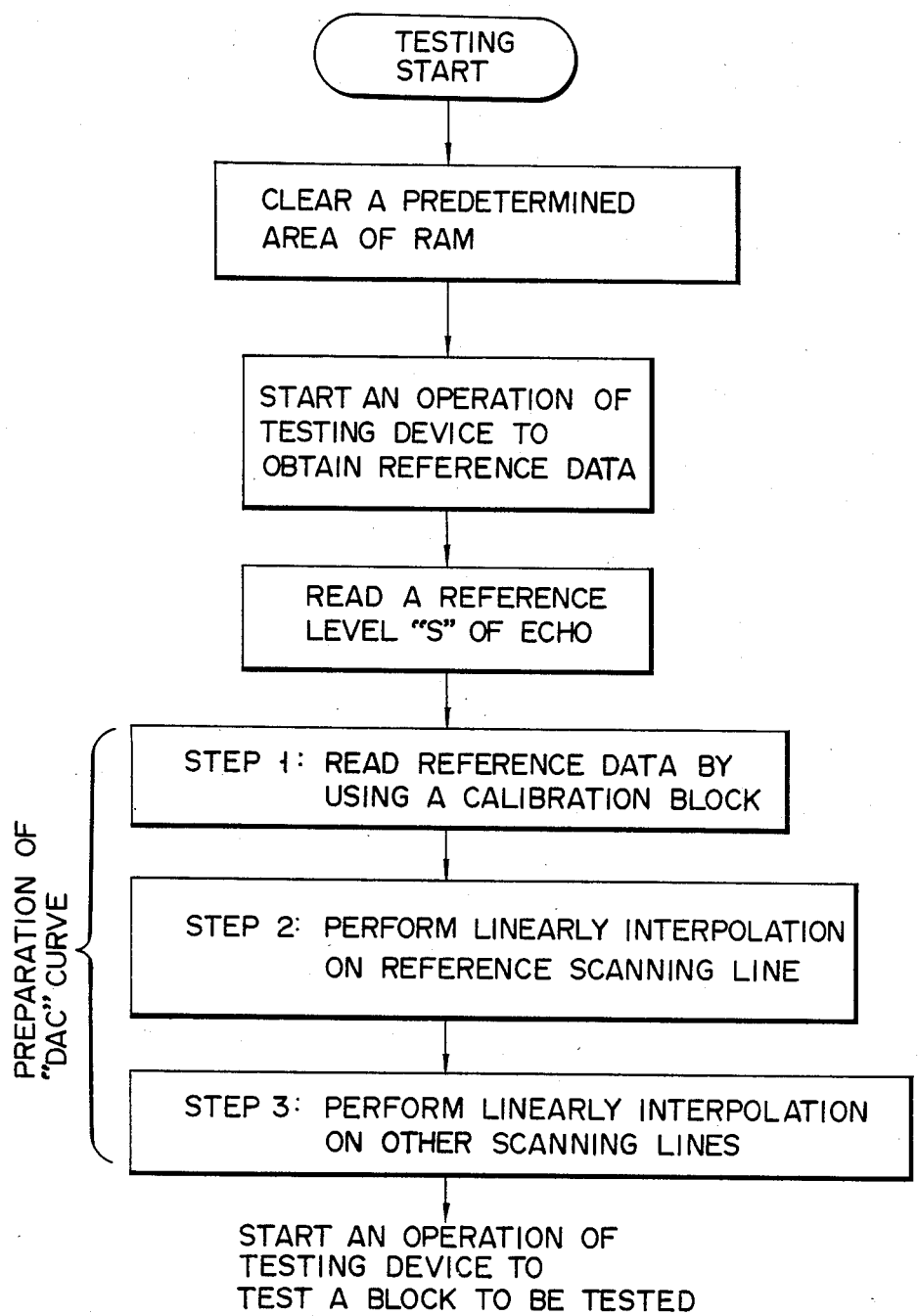

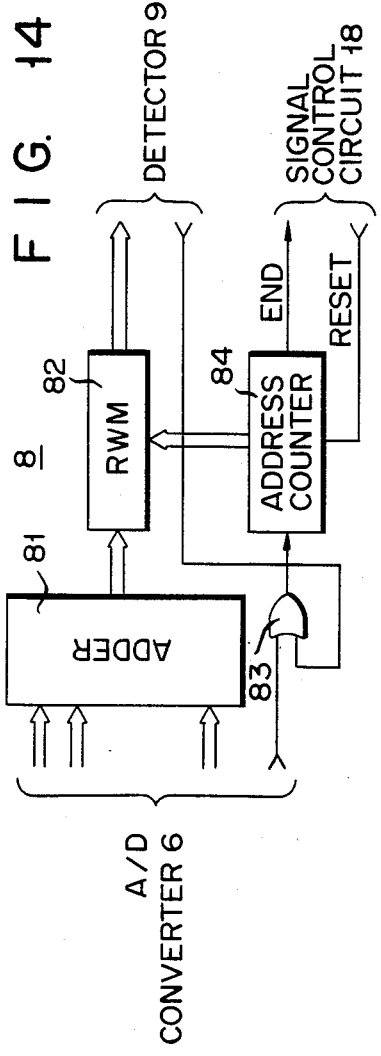
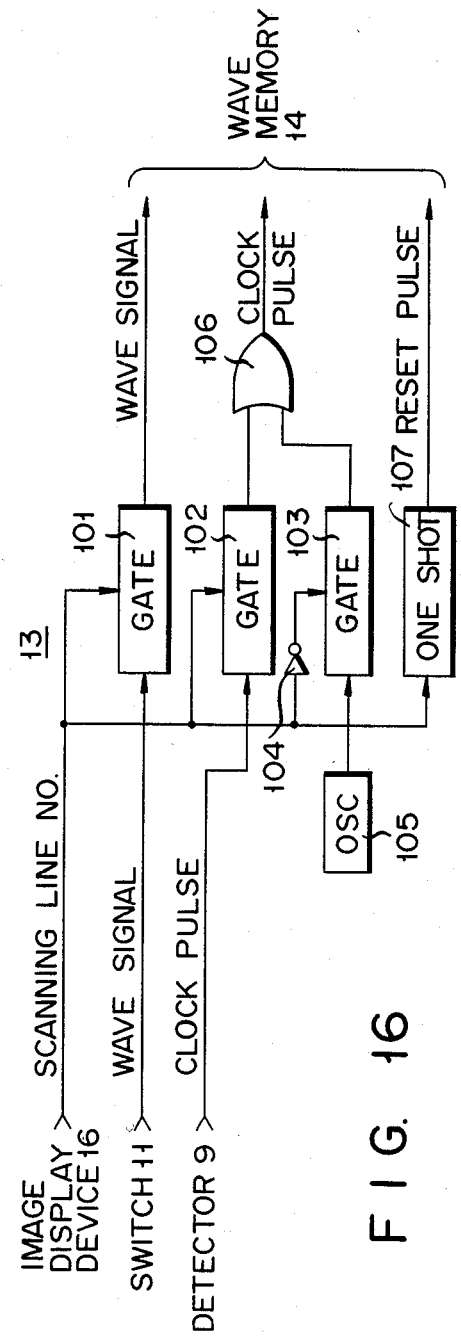

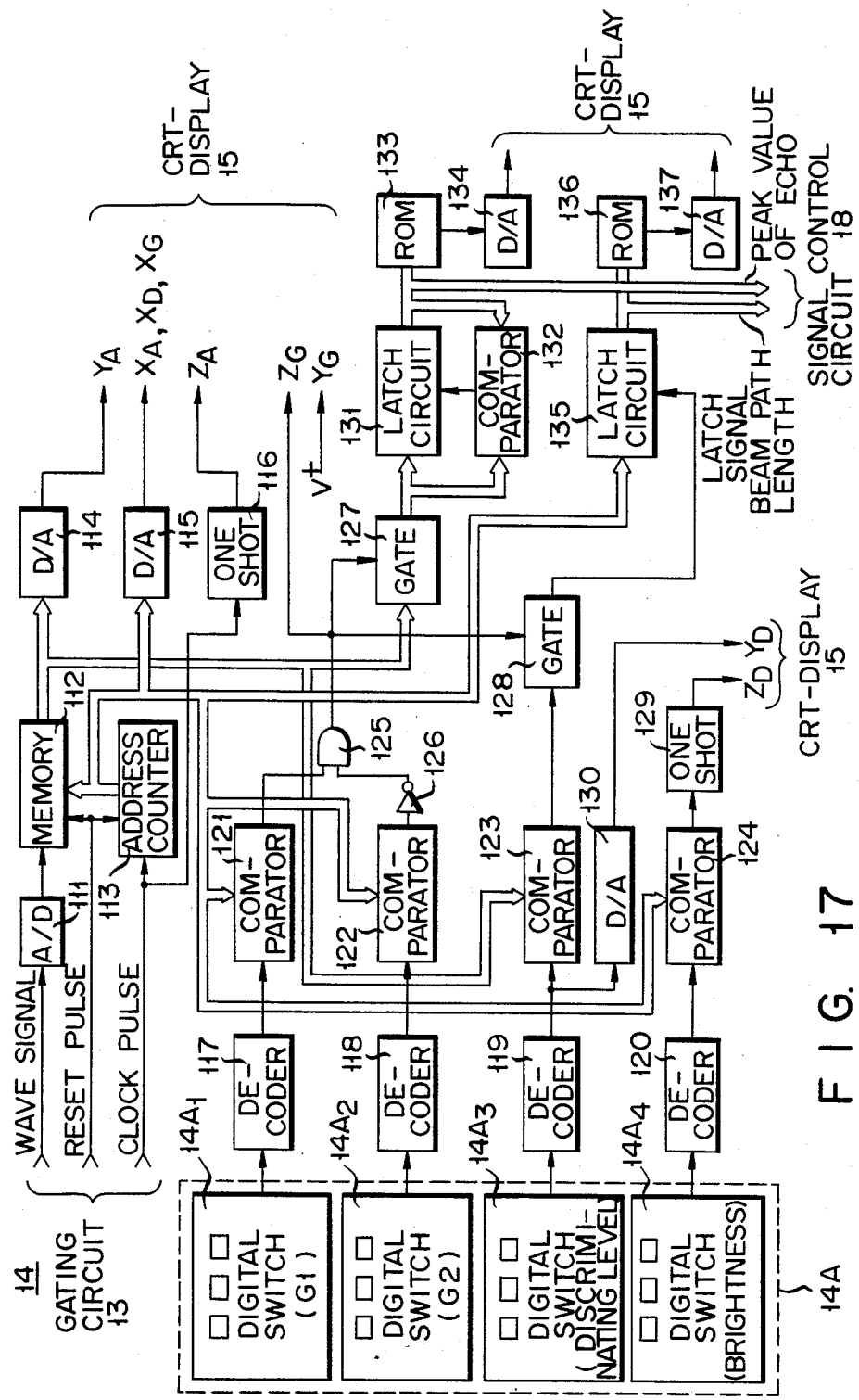
F I G. 17

ELECTRONIC SCANNING TYPE ULTRASONIC NON-DESTRUCTIVE TESTING APPARATUS

BACKGROUND OF THE INVENTION

The present invention relates to an electronic scanning type non-destructive testing apparatus which detects defects inside a structural member and displays the result of the defect detection.

The conventional ultrasonic non-destructive testing apparatus of this type, in the transmission mode, radiates ultrasonic waves by a plurality of transducers and focuses those waves into a single ultrasonic beam, which is transmitted in a desired direction on the basis of the principle of the phase interference of the ultrasonic waves radiated from the plurality of transducers through a control of the radiating timings of the ultrasonic waves. In the reception mode, the ultrasonic non-destructive testing apparatus receives ultrasonic echoes by a plurality of transducers, adds together the echo signals after a proper control of the delay times of the echo signals, and displays the added or intensified echo signal representative of the focused ultrasonic beam. The ultrasonic non-destructive testing apparatus is very useful because a tomogram of the member under defect inspection, viz. a B-scope image, is displayed in real time.

For a image display, the conventional ultrasonic non-destructive testing apparatus has employed a tonal display based on a strength or an amplitude of the echo signal or a bilevel display by setting up a level for discriminating an amplitude of the echo signal. For detecting size and configuration of a defect inside a structural member such as a metallic member, it is very important to accurately detect the location of the defect, and an amplitude, a waveform, and the like of the echo signal from the defect. The display method now employed, such as the tonal display or the bilevel display, does not provide an satisfactory accuracy in displaying the amplitude and the waveform of the echo signal.

The standard of ASME (American Society of Mechanical Engineers) requires the following judgment on the inspection of the defect in a structural member using a calibration block. An amplitude attenuation of the echo reflected from an actual member is corrected on the basis of an amplitude of the ultrasonic echo from a reference defect artificially formed in a reference member. An amplitude variation (amplitude attenuation) characteristic of the echo over the entire beam propagating path is obtained from the judgement through this correction work.

The conventional correction of the ultrasonic beam propagating path, as disclosed in U.S. Pat. No. 4,043,181, uses the amplitude characteristic of the received echo in the direction of only one ultrasonic beam propagating path for the attenuation correction of the echoes in every direction. Therefore, this correction method can not cope well variations in the amplitude characteristic of the ultrasonic beams in those different directions, resulting in degradation of the accuracy of the displayed image.

For the above reasons, it has been desired that the amplitude attenuation of the received echo signals in all the directions is accurately corrected, so as to ensure an exact display of an image of the inside of the structural member under defect inspection.

SUMMARY OF THE INVENTION

Accordingly, an object of the invention is to provide an ultrasonic non-destructive testing apparatus of the electronic scanning type which can accurately correct an amplitude attenuation of a received echo reflected from a body under defect inspection and hence display an exact image of a defect inside the body.

According to the invention, there is provided an ultrasonic non-destructive testing apparatus of the electronic scanning type comprising:

transmitter means for producing exciting pulses in response to a predetermined timing pulse;

a probe coupled to said transmitter means, having a plurality of transducers for transmitting ultrasonic waves into a body to be tested and for receiving ultrasonic echo waves;

signal processing means coupled to said probe for processing said ultrasonic echo waves received by said probe to generate an echo wave signal;

correcting means coupled to said signal processing means for correcting an amplitude attenuation of said echo wave signal by using a predetermined correction value at each crossing points in a two-dimensional coordinate to generate a corrected echo wave signal; and display means coupled to said correcting means for displaying a wave with regard to said body on the basis of the corrected echo wave signal.

According to the invention, there is further provided an ultrasonic non-destructive testing apparatus of the electronic scanning type comprising:

transmitter means for producing exciting pulses in response to a predetermined timing pulse;

a probe coupling to said transmitter means, having a plurality of transducers for transmitting ultrasonic waves into a body to be tested and for receiving ultrasonic echo waves;

signal processing means coupled to said probe for processing said ultrasonic echo waves received by said probe to generate an echo wave signal;

memory means coupled to said signal processing means for storing reference data on an amplitude attenuation of an ultrasonic echo coming through each beam propagating path which is obtained by transmitting the ultrasonic waves into a calibration body at the time of a calibration;

means coupled to said memory means for calculating a predetermined correction value on the basis of said reference data stored in said memory means, said predetermined correction value being at each crossing points on a two dimensional coordinate by applying a linear interpolation;

correcting means coupled to said signal processing means for correcting an amplitude attenuation of said echo wave signal by using said predetermined correction value at each crossing points to generate a corrected echo wave signal; and display means coupled to said correcting means for displaying a wave with regard to said body on the basis of the corrected echo wave signal.

BRIEF DESCRIPTION OF THE DRAWINGS

FIG. 1 shows a block diagram showing an embodiment of an ultrasonic non-destructive testing apparatus of the electronic scanning type according to this invention;

FIG. 4 is a flowchart to obtain a correction data map;

FIG. 14 is a functional diagram of an adder memory incorporated into the non-destructive testing apparatus shown in FIG. 1;

FIG. 16 is a functional diagram of a gating circuit for an A-scope display assembled into the non-destructive testing apparatus shown in FIG. 1;

FIG. 17 shows a block diagram of a wave memory for the A-scope display;

DETAILED DESCRIPTION OF THE PREFERRED EMBODIMENT

Figure 2A:
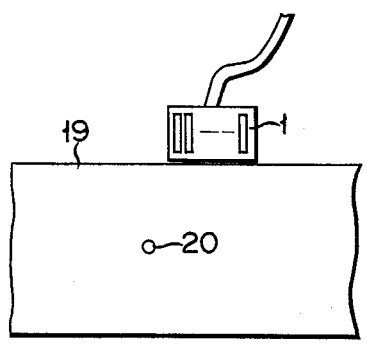
FIG. 2A is a diagram showing a probe placed on a body under defect inspection.

Referring to FIG. 1, there is shown in block form an embodiment of an ultrasonic non-destructive testing apparatus of the electronic scanning type according to this invention.

In FIG. 1, an ultrasonic probe 1 made up of a plurality of transducers is connected to an ultrasonic pulse transmitter 2 and an ultrasonic pulse receiver 3. The ultrasonic pulse transmitter 2 includes a plurality of transmitter units provided corresponding to the transducers of the probe 1. The ultrasonic pulse receiver 3 likewise includes a plurality of receiver units provided corresponding to the transducers. The transducer units transmit exciting pulses to the corresponding transducers, respectively. Upon receipt of the exciting pulses, the transducers radiate ultrasonic pulses, respectively. The ultrasonic pulse transmitter 2 is coupled to a delay timing pulse generator 4 which is comprised of a plurality of generator units provided correspondingly to the plurality of transmitter units. The generator units produce delay timing pulses for transmission to the transmitter units and control the generating timings of the exciting pulses from the transducer units. The generator units in the delay timing pulse generator 4 are respectively connected to A/D converter units constituting an A/D converter 6. Each receiver unit in the ultrasonic pulse receiver 3 convert the echo signal received by the probe 1 into an electrical signal. The receiver units in the ultrasonic pulse receiver 3 are respectively connected to amplifier units constituting an amplifier 7 which is contained in the delay adder 5. The amplifier units in the amplifier 7 respectively amplify the output electrical signals from the receiver units in the ultrasonic pulse receiver 3. The amplifier signals are input to the A/D converter units in the A/D converter 6 and are converted into digital signals under control of the delay timing pulse from the delay timing pulse generator 4. The A/D converted signals are then input to a digital adder memory 8 where these signals are added together. Thus, the delay adder 5 amplifies the analog signals from the ultrasonic pulse receiver 3, converts them into the digital signals in synchronism with the delay timing pulse, and adds together the converted signals to generate a sum signal of the echo signals. An amplitude of the amplifier 7 is controlled by the signal derived from a signal control circuit 18. The delay adder 5 is connected to an envelope detector 9. In the envelope detector 9, the sum signal from the delay adder 5 is converted into an analog signal and then is subjected to an envelope detection. The envelope detector 9 is connected to a correcting circuit 10 which is for correcting an attenuation of a strength or an amplitude of the echo signal with regard to the ultrasonic beam path length. The outputs of the envelope detector 9 and the correcting circuit 10 are both connected to an A-scope display 12, by way of a switch 11. This switch 11 selects the output signal from the envelope detector 9 or the correcting circuit 10 and supplies the selected one to the A-scope display 12. The A-scope display 12 is comprised of a gating circuit 13 connected to the envelope detector 9 or the correcting circuit 10 through the switch 11, a wave memory 14 for fetching the echo signal from the envelope detector 9 or the correcting circuit 10, and a CRT-display 15 for visualizing the echo signal coming from the wave memory 14. The wave memory 14 stores data of a range set on the beam propagating path and data of a discriminating level for discriminating a strength of the echo wave signal in the set range. The set range and the discriminating level are displayed on the screen of the display 15. The display 15 further displays a maximum strength of the echo wave signal in the set range and a location of the echo wave signal on the beam propagating path where the echo wave signal exceeds the discriminating level. The correcting circuit 10 is connected to an image display device 16 which receives the output signal from the correcting circuit 10, and displays a B-scope image. The image display device 16 displays an ultrasonic wave propagating path for a predetermined transmission/reception ultrasonic wave in the form of an intensity signal. For the intensity display, the apparatus receives a signal representing that the propagating path of the ultrasonic beam coming from the probe 1 is coincident with the predetermined beam propagating path. And the scanning line of the display 15 corresponding to the coincident beam propagating path (scanning line) is subjected to an intensity modulation. The signal control circuit 18 controls various operations; setting a delay time for the delay timing pulse generator 4, setting an amplitude of the amplifier 7, setting a correction value for the correcting circuit 10, the operation of the gating circuit 13, the data input to the A-scope display 12 and the operation timing of the A-scope display 12, and the read/write operation of data for the RAM 17.

Figure 2C:
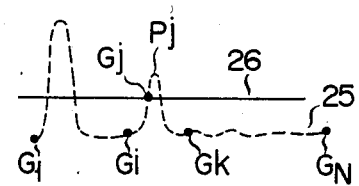
FIG. 2C shows a waveform of an ultrasonic beam echo.
Figure 2B:
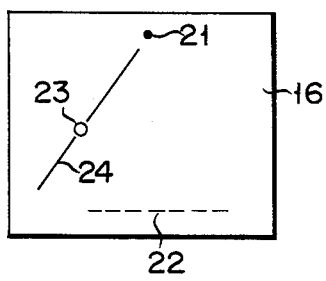
FIG. 2B is a diagram showing a B-scope image of the inside of the body under defect inspection.
Figure 2D:
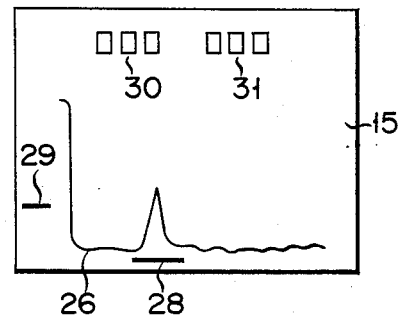
FIG. 2D shows an A-scope image of the body under defect inspection.

The operation of the ultrasonic non-destructive testing apparatus will be described. The non-destructive testing apparatus is operated under a condition that the probe 1 is placed on a body 19 to be tested i.e. under defect inspection, for example, a structural member, as shown in FIG. 2A. When the apparatus starts up, the delay timing pulse generator 4 produces timing pulses to the ultrasonic pulse transmitter 2. In synchronism with this timing pulse, the ultrasonic pulse transmitter 2 produces exciting pulses with different delay times toward the individual transducers of the probe 1. Upon receipt of the exciting pulses, the transducers of the probe 1 transmit ultrasonic waves into the structural member 19. In this case, the transducers are excited with different time delays so that the ultrasonic waves radiated from the probe 1 are focused into a single ultrasonic beam. The sequential order for exciting the transducers are successively changed every excitation of the probe 1, so that the ultrasonic beam path is deflected in a sectorial fashion. The echo of the ultrasonic beam traveling on the propagating path in the structural member 19 is received by each of the transducers in the probe 1 every exciting of the probe 1 and is converted into an electrical signal. The echo wave signals as the electrical signals are input to the corresponding amplifier unit in the amplifier 7, respectively. The echo wave signal amplified are further applied to the A/D converter units in the A/D converter 6, respectively. The A/D converted signals are applied to the digital adder memory 8 where those are added together into a signal representing the echo wave of the single ultrasonic beam transmitted. The echo wave signal is applied to the envelope detector 9 where it is subjected to the A/D conversion and the envelope detection. When the switch 11 is turned to the contact A, the envelope detected signal is supplied to the gating circuit 13 and under control of the signal control circuit 18 stored into the wave memory 14. The echo wave signal stored in the wave memory 14 is read out and displayed as an A-scope image 26 on the screen of the CRT-display 15, as shown in FIG. 2D. The wave memory 14 further stores the data of the range set on the beam traveling path and the data representing a discriminating level of an amplitude of the echo wave signal. The range 28 and the discriminating level 29 are intensity-modulated and displayed on the screen of the display 15, as shown in FIG. 2D. The display 15 further displays in the display windows 30 and 31 numerals representing a maximum echo amplitude $P_j$ within the range and a position $G_j$ of the echo wave signal where the echo wave signal exceeds the discriminating level within the range, as shown in FIG. 2C.

The output signal from the envelope detector 9 is also input to the correcting circuit 10. The correcting circuit 10, under control of the signal control circuit 18, corrects an attenuation of the echo signal from the envelope detector 9, which is caused in the course of its propagation. The corrected signal is then input to the image display device 16 where it is displayed as a B-scope image, as shown in FIG. 2B. The image display device 16 displays a start point 21 of the ultrasonic beam, a scanning line signal 24, a defective signal 23 representing a defective part 20 in the structural member 19 and a reflecting signal 22 reflected at the bottom of the structural member 19. The outline of the operation of the ultrasonic non-destructive testing apparatus of the electronic scanning type shown in FIG. 1 is as mentioned above.

How to obtain a distance amplitude correction (DAC) curve applied for an amplitude characteristic on the beam propagating path, viz. a correction data map, will be described referring to FIGS. 3A and 3B, and FIGS. 4 to 10.

Figure 3A:
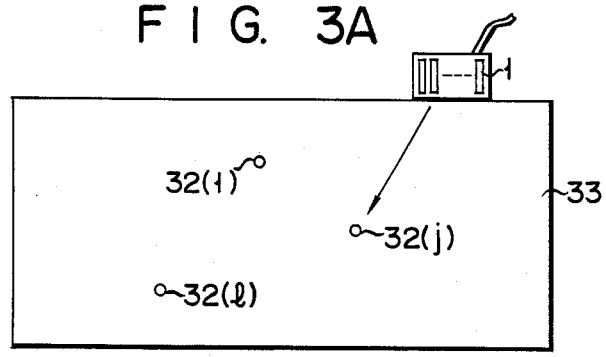
FIG. 3A illustrates a probe placed on a reference body under defect inspection.
Figure 3B:
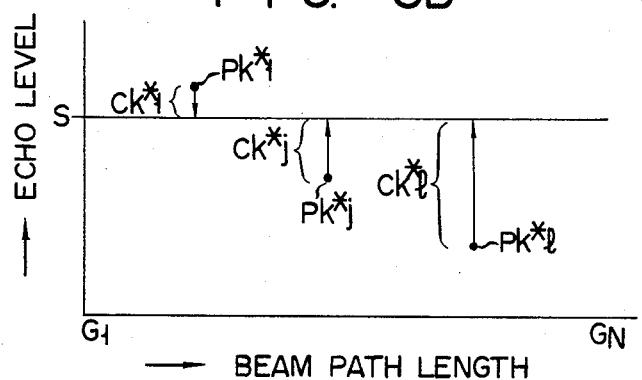
FIG. 3B illustrates a relationship between the level of ultrasonic echoes versus the beam path length.

For preparing the DAC curve, a reference structural member 33 is used in which defects $32_1$, $32_j$ and $32_l$ are artificially formed, as shown in FIG. 3A. If the artificial defects $32_1$, $32_j$ and $32_l$ have the same size, the maximum amplitudes of the echo are inversely proportional to the distance from the probe 1 to the artificial defects $32_1$, $32_j$ and $32_l$, as shown in FIG. 3B. Therefore, a ratio of each of the maximum amplitudes $P^*_{k1}$, $P^*_{kj}$ and $P^*_{kl}$ of the echoes to a reference value S, i.e. $C^*_{kj}=S/P^*_{kj}$, is a correction value at a position $G^*_{kj}$.

In the procedure for preparing the DAC curve, a first step is to clear a given memory area in the RAM 17, as shown in a flowchart of FIG. 4. A second step is to place the probe 1 on the structural member 33 and to start up the ultrasonic non-destructive testing apparatus under this condition. Then, an operator manually loads a reference echo level S, which has theoretically been obtained with respect to the artificial defects $32_1$, $32_j$ and $32_l$, into the RAM 17 through key-in operation on a key board (not shown). Subsequently, steps S1 to S3 are executed in successive manner. In the step S1, a scanning line number (a beam propagating path number) from which the reference data will be obtained is selected and the ultrasonic waves are transmitted. Detection is then made of strength of the echoes coming from the reference locations of the reference defects through the reference propagating paths. In a second step, detection is made of strength of the echoes at other locations than the reference locations on the reference propagating paths. In the third step S3, detection is made of strength of the echoes at the individual locations on other propagating paths than the reference ones. Step 1 is executed according to the following procedure. A first procedural step is to read reference scanning line number $L^*_k$ from which the reference data is obtained. To read this, the reference scanning line number $L^*_k$ or the beam propagating paths set through the digital switch operation by an operator is loaded into the RAM 17 of the signal control circuit 18. At the predetermined reference locations of a scanning line number, number "j" are assigned to the individual reference data of the reference defects, through key board operation by an operator. In this numbering, the youngest number is assigned to the reference data at the shortest distance, that is, closest to the probe 1. The number assigned to the data is older as the distance on the data is longer. Then, the probe 1 is moved so that the reference scanning line displayed by the image display device 16 is located above each reference defect of the reference data numbered on the basis of the reference scanning line. In this way, the echo from the reference defect is maximized.

Figure 6:
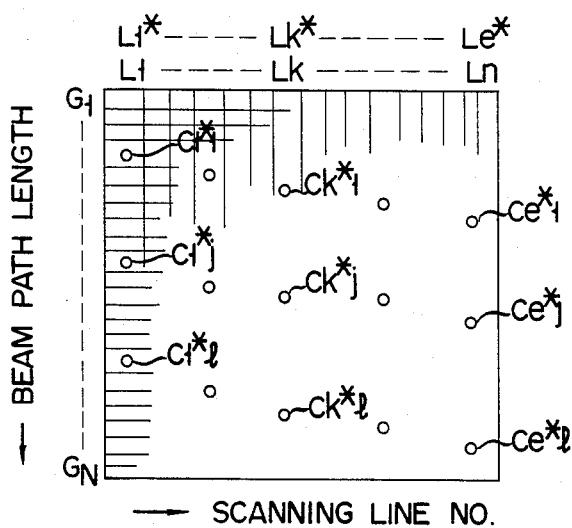
FIG. 6 shows a data map obtained through the process of the first step.
Figure 5:
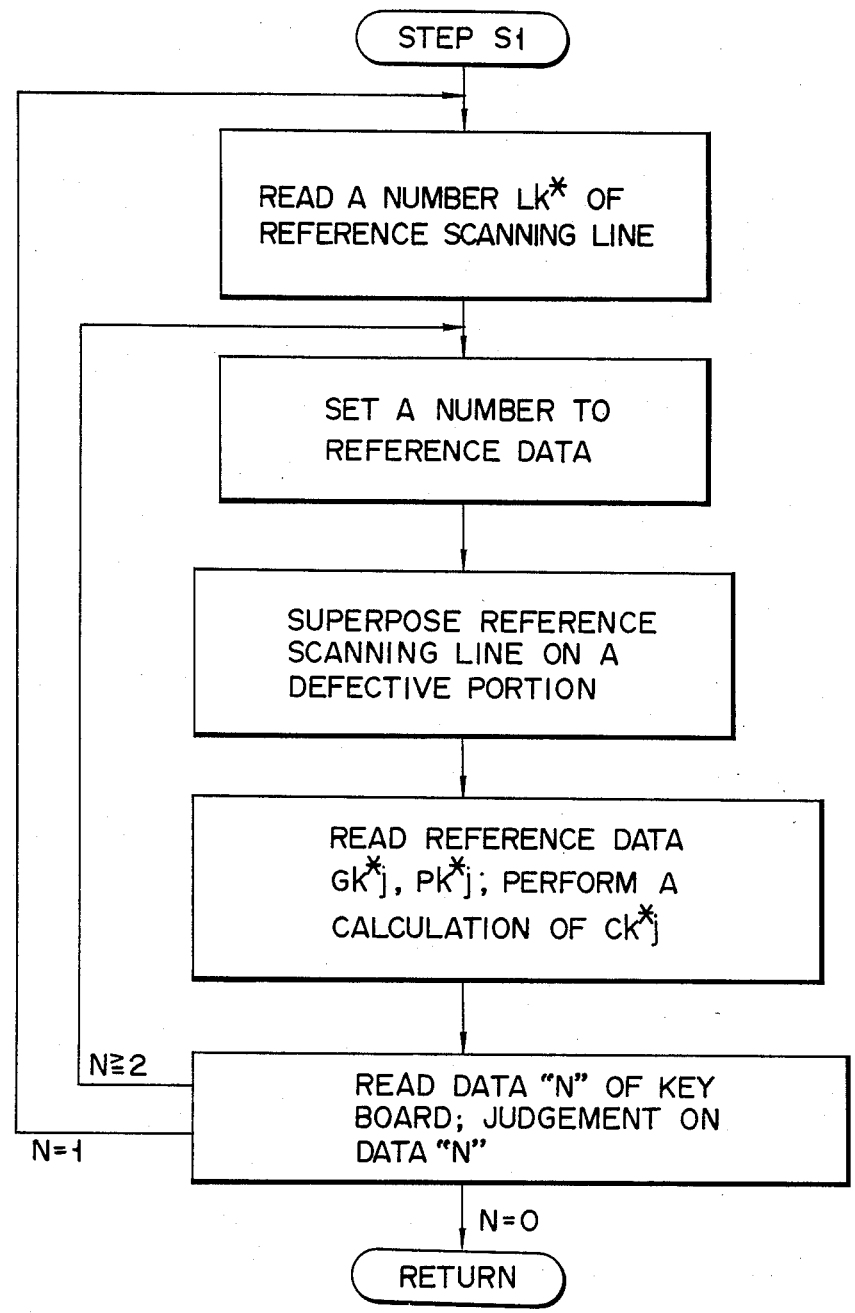
FIG. 5 shows a detailed flowchart of a first step for obtaining the correction data map.

The following step is to fetch the location providing a maximum beam propagating path and the data at this location (i.e. the reference data or the maximum echo value), and to calculate a correction value $C_{kj}^*$ at this location. To effect this, by operating the switch SW of the signal control circuit 18, the peak value $P_{kj}^*$ latched and the location $G_{kj}^*$ on the beam propagating path are fetched. And a relation $C_{kj}^* = (S/P_{kj}^*)$ for obtaining the correction value $C_{kj}^*$ is worked out using this data fetched. The $G_{kj}^*$ and $C_{kj}^*$ are written into the RAM 17 (FIG. 6). The following judgement follows the writing operation. The judgement is: Is the fetching of the reference data is completed (N=0?) ?; Is it necessary to change the scanning line from which the data is obtained (N=1?) ?; and is it necessary to fetch the other reference data on the same scanning line (N≧2) ? When N=1, viz. the scanning line must be changed, the processing returns to the start in this routine and a new reference scanning line is read. When N≧2, viz. the other reference data must be fetched, the processing returns to the step to set a reference data number. When N=0, viz. the fetching operation ends, the processing advances to the step S2.

Through the above steps, the reference data at the predetermined locations on all of the reference scanning lines $L_1^*, \ldots, L_e^*$ are fetched and the correction values $C_{11}^*, \ldots, C_{el}^*$ at those locations are calculated (FIG. 6).

Figure 7:
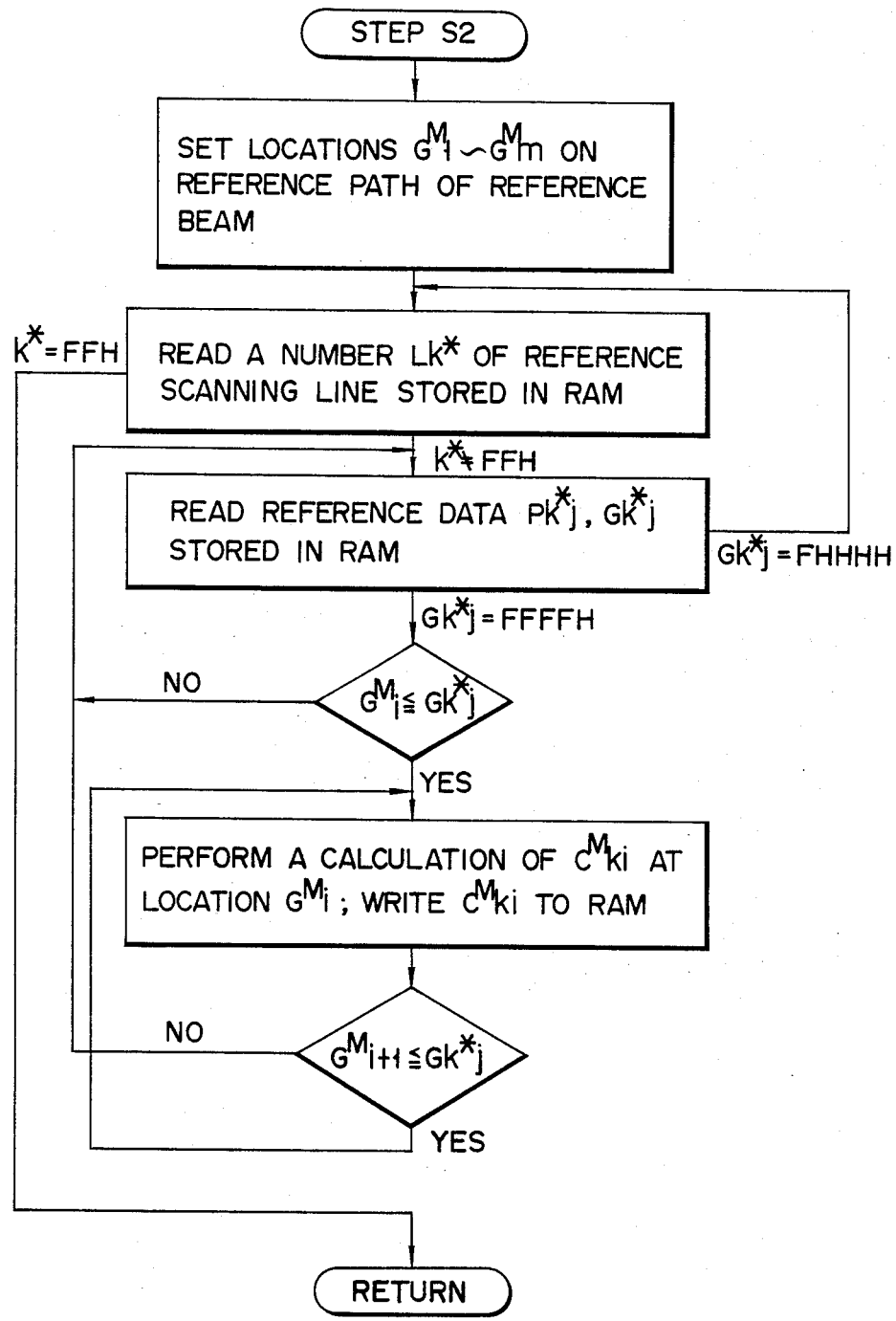
FIG. 7 shows a detailed flowchart of a second step for obtaining the correction data map.
Figure 8:
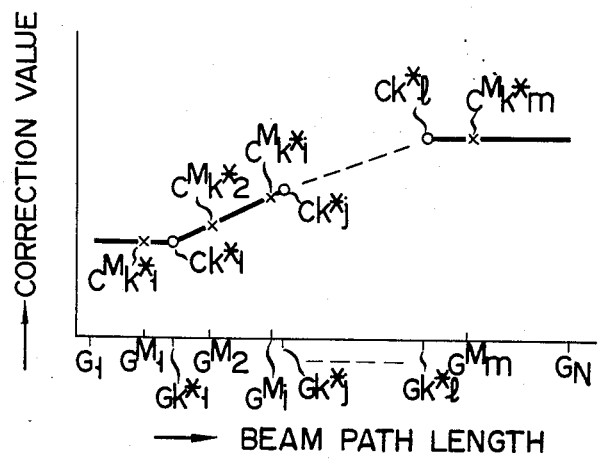
FIG. 8 shows an interpolation data map obtained by a linearity interpolation on each beam path.

The procedure in the second step S2 will be described referring to FIGS. 7 and 8.

In this step S2, a first procedural step is to set a reference scanning line number or a beam propagating path number $L_k^*$, and the locations $G_1^M, \ldots, G_m^M$ on the beam propagating paths from which the correction values are obtained. This is done by writing a beam propagating path number $L_k^*$, and the locations $G_1^M, \ldots, G_m^M$ into the RAM 17. This writing operation is done by manually operating necessary keys on the key board by an operator. Then, the reference scanning line number $L_k^*$ is read out from the RAM 17. At the initial stage of the system operation, the RAM 17 is in a clear state. At instance that the RAM area not storing the reference scanning line number is accessed, the read-out of the reference scanning line number ends. Then, the reference data $C_{kj}^*$ at the locations $G_{kj}^*$ on the reference beam propagating paths stored in the RAM 17 are read out. Succeedingly, it is checked whether or not $G_i^M \leq G_{kj}^*$. If the result of the check is NO, the processing returns to the step to read out the reference data $C_{kj}^*$ at the location $G_{kj}^*$ stored in the RAM 17. When the result is YES, a step to be executed is to work out the operation for obtaining the correction value $C_{ki}^*$ at the location $G_i^M$, and the writing operation of the calculated correction value $C_{ki}^*$ into the RAM 17. If $G_{kj}^* < G_i^M$, the correction value $C_{kj}^*$ is written as $C_{km}^*$ into the RAM area storing the $L_k^*$ and $G_{kj}^*$. The correction value $C_{ki}^*$ at the location $G_i^M$ can be obtained using the following equation.

$$C_{ki} = [(C_{k(i-1)}^* - C_{kj}^*)/(G_{k(i-1)}^* - G_{kj}^*)] \times (G_{k(j-1)}^* - G_i^M) + C_{k(i-1)}^*$$

The correction value $C_{ki}^M$ is written into the memory location of the RAM 17 for the reference scanning line number $L_k^*$ and the location $G_i^M$. When the reference data $C_{k(j-1)}^*$ at the location $G_{k(j-1)}^*$ is not present, $C_{ki} = C_{kj}^*$. The correction value $C_{ki}^*$ is written into the RAM 17 and then the judgement of $G_{i+1}^M \leq G_{kj}^*$ is performed. When the result of the judgement is NO, the processing returns to the step to read out the reference data $C_{kj}^*$ at the location $G_{kj}^*$. When the result is YES, the step to be executed is to perform the operation to obtain the correction value $C_{k(i+1)}^M$ at the location $G_{(i+1)}^M$ and to write the calculated value $C_{k(i+1)}^M$ into the RAM 17. When the "k" of the scanning line number $L_k^*$ stored into the RAM 17 is equal to FFH in hexadecimal code, viz. k=FFH, the second step S2 ends and the third step is executed.

Figure 10:
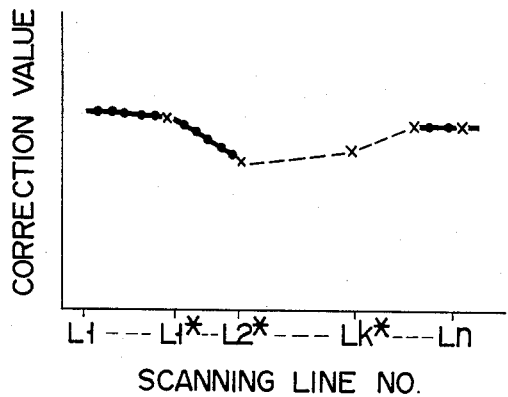
FIG. 10 shows a correction data map between the adjacent reference scanning lines in the scanning direction.
Figure 9:
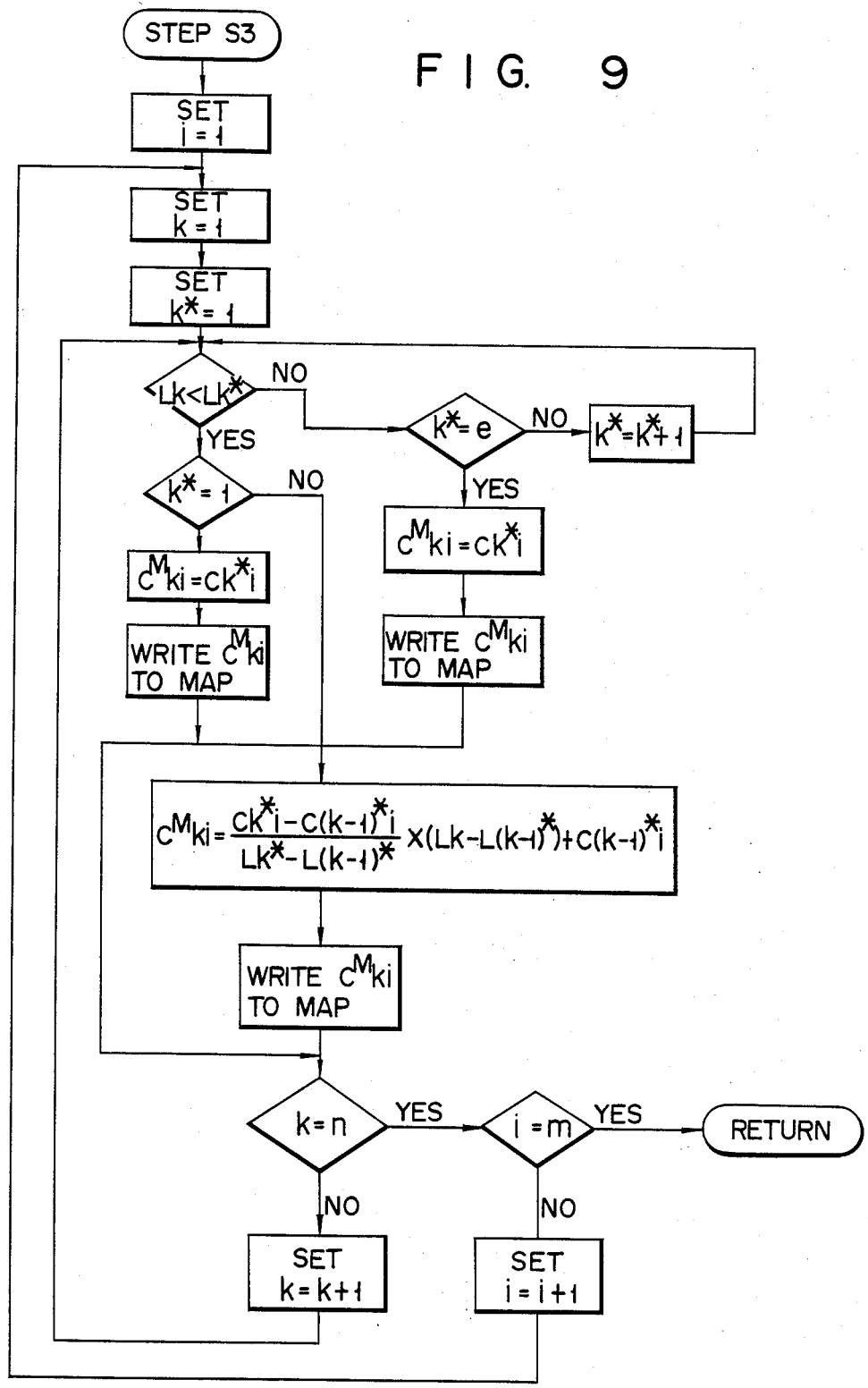
FIG. 9 shows a detailed flowchart of a third step for obtaining the correction data map.

The program of the step S3 will be given referring to FIGS. 9 to 10.

In this step, firstly, "i" of the location $G_i$ for specifying the ordinates of a desired memory location from which the data is obtained is set to 1, viz. i=1. Then, "k" of $L_k^*$ (representing a number for a desired provisional beam propagating path for defining the abscissa of the desired location is set to 1, viz. k=1.

Then, $L_k^* < L_k^*$ is checked. If its result is YES, it is further checked whether k is 1 or not and whether or not the k set is the smallest value of the reference scanning line number. If the result of the check is YES, $C_{ki}^*$ is loaded as $C_{ki}^M$ into the RAM location defined by the provisional beam propagating path $L_k^*$ and the ordinate $G_i^*$. In this way, the linear interpolation is performed for the scanning line, as shown in FIG. 10. Then, check is made as to whether or "k" is its maximum value "n". Further, check is made as to whether or not the correction values at the intersections of all the provisional beam propagating paths to the ordinate point $G_i$ are calculated and the calculated one is stored. When the result of the check is NO, "k" is set to k+1 and the step of $L_k < L_k^*$ is then executed. On the other hand, when the result is YES, it is checked whether or not "i" takes its maximum value "m". Further, check is made as to whether the correction values are stored in all the locations on the provisional beam propagating paths, which are set up as the locations for obtaining the correction values. If the result is NO, the program flows back to the step to set "k" to 1, viz. k=1. If it is YES, the step 3 ends. If, in the step of $L_k < L_k^*$, the result of the check is NO, it is checked whether or not k takes its maximum value, that is, whether or not the numbers of all the scanning lines $L_k^*$ is read out. If the result is NO, k is set to k+1 and the program flows back to the step of $L_k < L_k^*$. On the other hand, if it is YES, the correction value $C_{ki}^*$ is written as $C_{ki}^M$ into the RAM 17. Following the write operation, the process flows to the step to see if k=0.

In the step to see if k=1, where the result of the check is NO, the processing advances to the step to calculate the correction value $C_{ki}^*$. The correction value $C_{ki}^*$ is calculated using the equation of $$C_{ki}^M = \frac{C_{ki}^* - C_{(k-1)i}}{L_k^* - L_{(k-1)}^*} \times (L_k - L_{(k-1)}^*) + C_{(k-1)i}$$

The calculated correction value $C^*_{ki}$ is written into the RAM 17. Following this write step, the processing advances to the step to see if k=n. In this way, the processing of the step 3 is completed, the correction data at all the intersections of a plurality of locations $G^*_k$ and $G_k$ on the ordinate to the reference beam propagating path $L^*_k$ and the provisional beam propagating path $L_k$ are written into the RAM 17. Thus, the DAC curve is stored into the RAM 17. When the structural member 19 is actually subjected to an actual defect inspection by using the ultrasonic non-destructive testing apparatus shown in FIG. 1, the amplitude attenuation of the echo wave can be corrected by multiplying the echo data on each ultrasonic beam propagating path by the correction data read out from the corresponding RAM location. Therefore, the accuracy of an image displayed on the display is remarkably improved.

Detailed arrangements of the functional components in the ultrasonic non-destructive testing apparatus shown in FIG. 1 will be described hereinafter.

Figure 11:
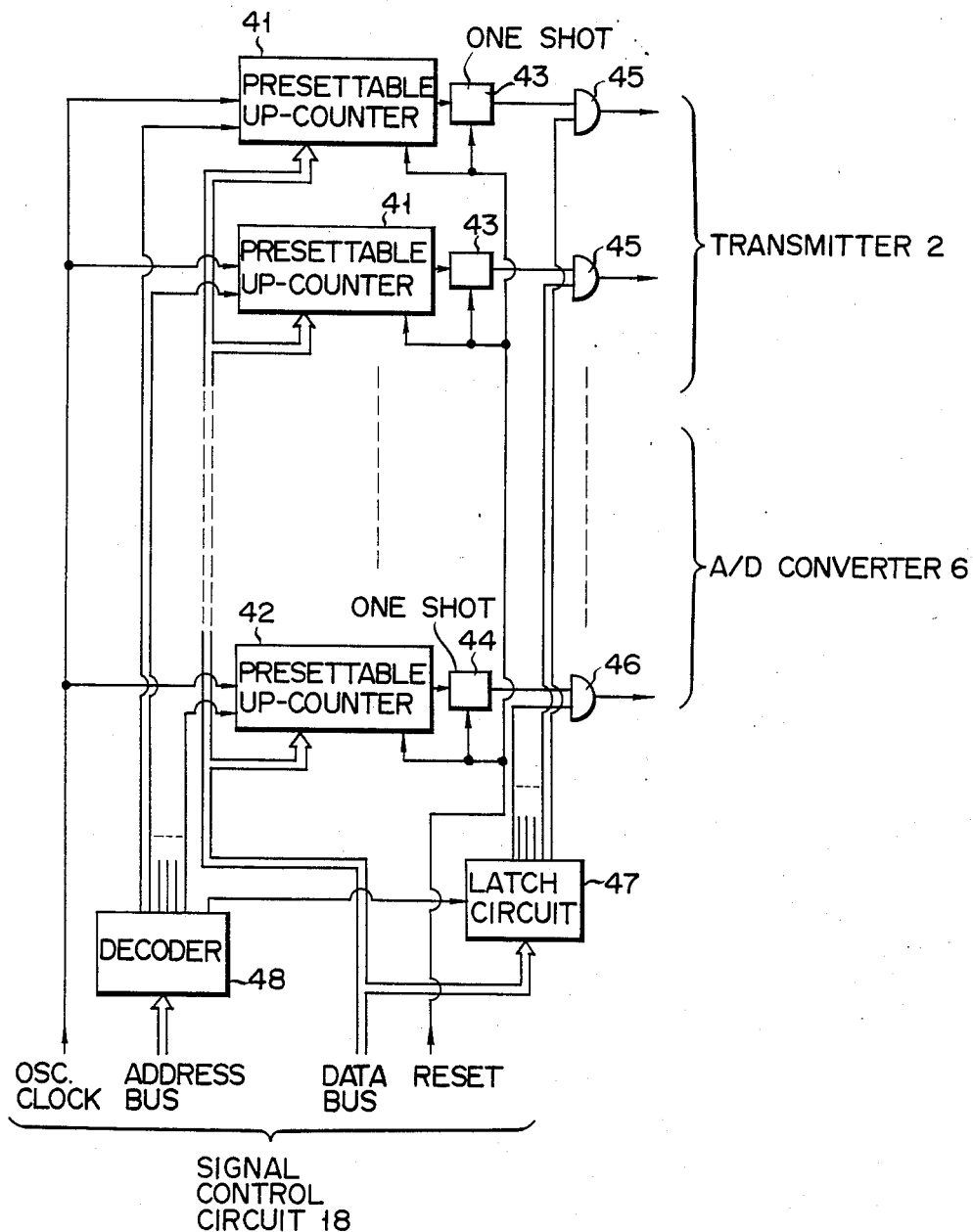
FIG. 11 shows a functional diagram of a delay timing pulse generator incorporated into the non-destructive testing apparatus of FIG. 1.

FIG. 11 shows a detailed arrangement of the delay timing pulse generator 4.

Presettable up-counters 41 are provided with the number equal to that of the transducers constituting the probe 1. Presettable up-counter 42 are provided with the number equal to that of the A/D converter units of the delay adder 5. The signal control circuit 18 applies the delay time data as the preset signal over the data bus and the address signal over the address bus to the presettable up-counters 41 and 42. The signal control circuit 18 further supplies a clock signal and a reset signal to the presettable up-counters 41 and 42. The counts of the presettable up-counters 41 and 42 are set in one-shot MMs (multivibrators) 43 and 44, respectively. The one-shot MMs 43 and 44 are further supplied with a reset signal from the signal control circuit 18. The output signals from the one-shot MMs 43 and 44 respectively are applied to the input terminals of AND gates 45 and 46, each of which are one of the input terminals. The data from the signal control circuit 18 is input via the data bus to a latch circuit 47 where it is latched. A decoder 48 supplies a latch signal to the latch circuit 47. The output signal from the latch circuit 47 is applied to the other input terminals of the AND gates 45 and 46. The output signals of the AND gates 45 are input to the transmitter units of the ultrasonic pulse transmitter 2. The output signals from the AND gates 46 respectively are input to the A/D converter units of the A/D converter 6.

The data which differ from one another by the given delay times are preset in the presettable up-counter 41. This is true for the presettable up-counter 42.

The presettable up-counter 41, when counting the clock pulses by the data preset, produces an output signal. Accordingly, the presettable up-counter 41 successively produces pulse signals with different given delay times and applies them to the transmitter units. The presettable up-counter 42 operates in a similar way to produce pulse signal with different given delay times for transmission to the A/D converter units.

Figure 12:
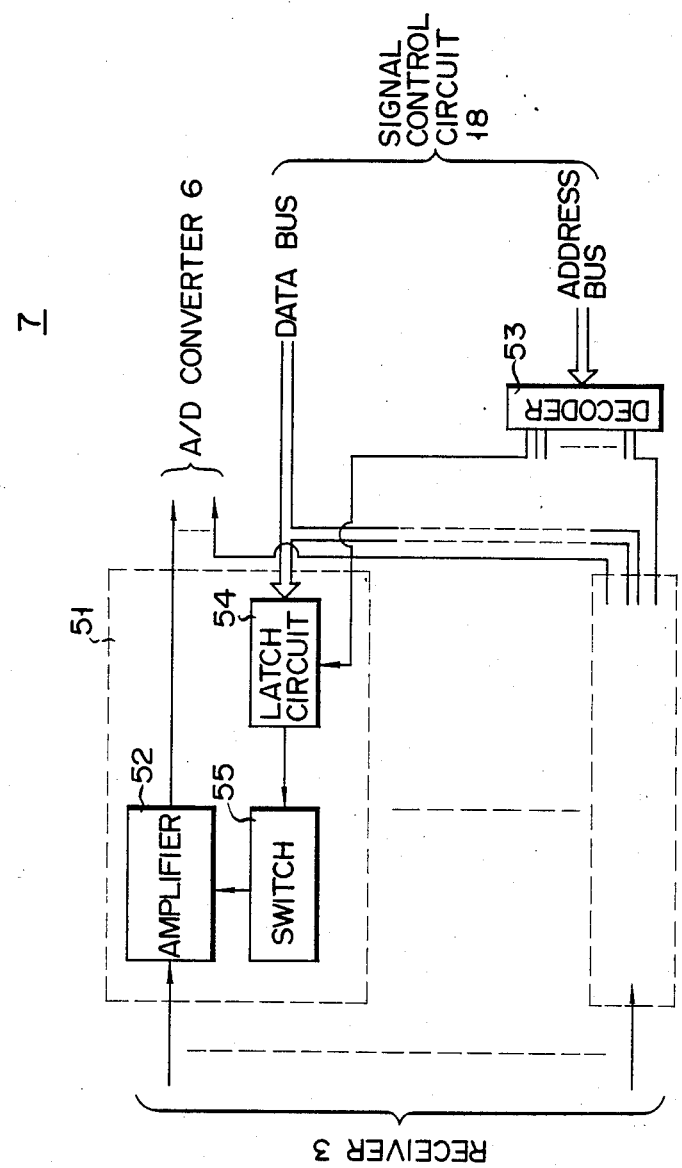
FIG. 12 shows a functional diagram of an amplifier incorporated into the non-destructive testing apparatus shown in FIG. 1.

FIG. 12 shows a detailed arrangement of the amplifier 7 in the delay adder 5. As described earlier, the amplifier 7 contains a plurality of amplifier units which are provided corresponding to the transducers of the probe 1. However, only one amplifier unit 51 will be described, for simplicity and for all of the amplifier units have the same arrangements. An amplifier 52 of the amplifier unit 51 is supplied with an echo signal as an electrical signal from the transmitter unit corresponding to the amplifier unit 51. The amplifier 52 amplifies the signal input with a given amplitude. The amplified signal is input to the corresponding A/D converter unit of the A/D converter 6 of the delay adder 5. The address signal is input from the signal control circuit 18 to the decoder 53, through the address bus. The decoder 53 decodes the address signal applied thereto. The decoded signal is input as a latch signal to the latch circuit 54. The data representative of an amplitude is applied from the signal control circuit 18 over the data bus to the latch circuit 54 where it is latched. The output signal from the latch circuit 54 is input to a switch circuit 55. The output signal from the switch circuit 55 is input to the amplifier 52.

Figure 13:
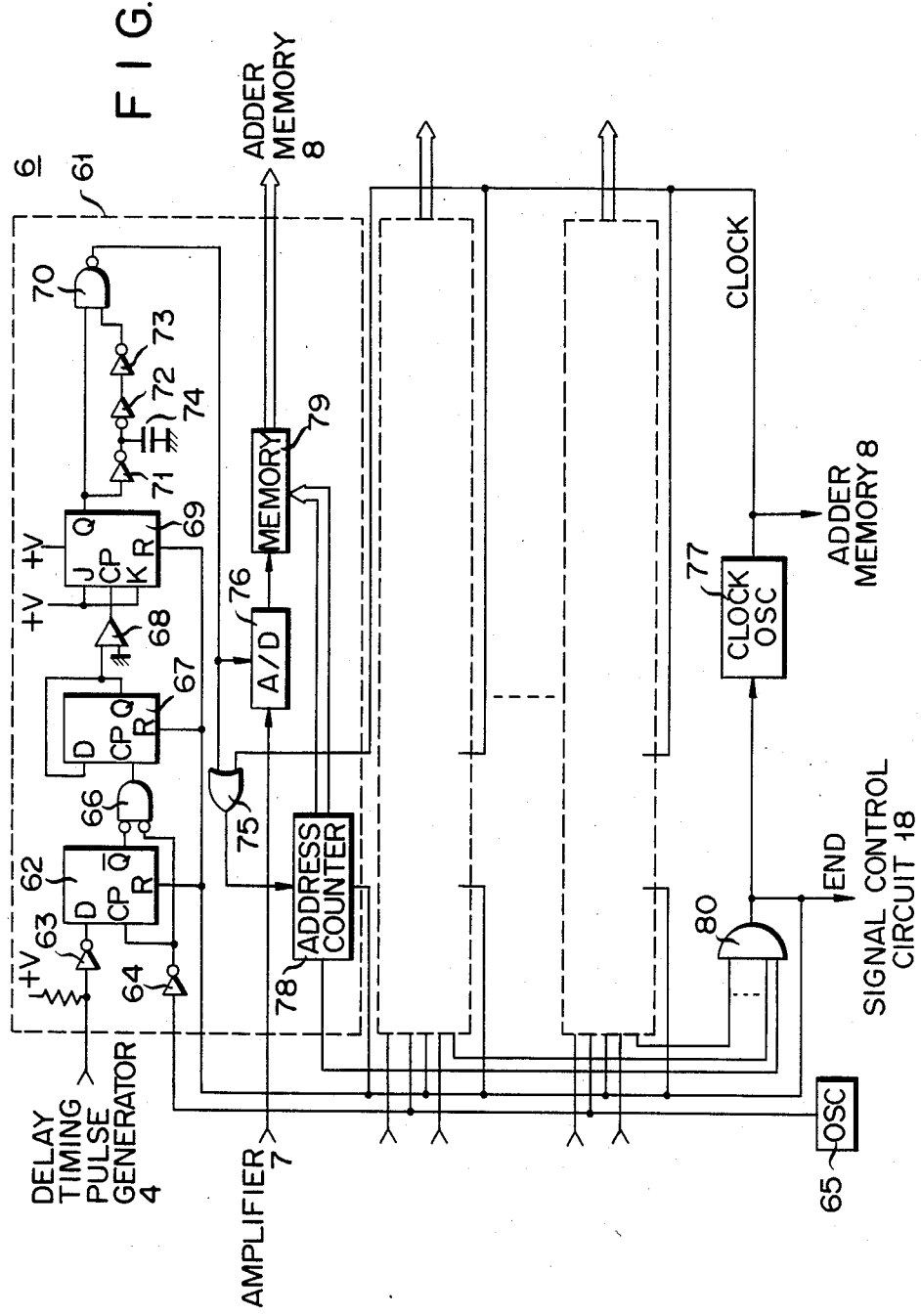
FIG. 13 shows a functional diagram of an A/D converter incorporated into the non-destructive testing apparatus shown in FIG. 1.

FIG. 13 shows a practical arrangement of the A/D converter of the delay adder 5.

The A/D converter 6 is comprised of a plurality of A/D converter units which are provided corresponding to the amplifier units of the delay adder 5. Since the A/D converter units have the same arrangements, only the A/D converter unit 61 will be described as a typical example.

A signal is applied from the delay timing pulse generator 4 to the D terminal of a flip-flop 62, through an inverter 63. A clock pulse is applied from an oscillator 65 to the CP terminal of the flip-flop 62, through an inverter 64. The $\overline{Q}$ output of the flip-flop 62 is input to one of the input terminals of a NAND gate 66. A clock pulse is applied from the oscillator 65 to the other input terminal of the NAND gate 66, through the inverter 64. The output signal from the NAND gate 66 is input to the CP terminal of a flip-flop 67. The input terminal of the flip-flop 67 is connected to the $\overline{Q}$ output terminal. The $\overline{Q}$ output terminal of the flip-flop 67 is connected to one of the input terminals of a comparator 68. The other input terminal of the comparator 68 is grounded. The output terminal of the comparator 68 is connected to the CP terminal of a flip-flop 69. The J terminal and the K terminal of the flip-flop flop 69 are coupled with +V potential. The $\overline{Q}$ output terminal of the flip-flop 69 is directly connected to one of the input terminals of a NAND gate 70. The Q output terminal of the flip-flop 69 is connected to the other input terminal of the NAND gate 70, through three inverters 71 to 73 which are connected in series. A capacitor 74 is inserted between a junction of the first to second inverters 71 and 72 and ground. The output signal of the NAND gate 70 is input to one of the input terminals of an OR gate 75 and to an A/D converter 76. A clock signal from a clock oscillator 77 is input to the other input terminal of the OR gate 75. The output terminal of the OR gate 75 is connected to an address counter 78. The A/D converter 76 is impressed with the output signal from the corresponding amplifier unit in the A/D converter 6. The A/D converter 76 converts the output signal from the amplifier circuit into a digital form. The A/D converted signal is input to and stored into a memory 79. The data stored in the memory 79 is input to the digital adder memory 8. The first output signal of the address counter 78 is input as an address signal to the memory 79. The second output signal from the address counter 78 is input to an AND gate 80. The AND gate 80 is supplied with the output signals from the address counters of all other A/D converter units (not shown). The AND gate 80 produces a signal to indicate the clock oscillator 77 to start up, and sends an END signal to the signal control circuit 18. The AND gate 80 further sends a reset signal to the R terminals of the flip-flops 62, 67 and 69.

The memory 79 of the A/D converter unit 61 in the A/D converter thus arranged stores an echo signal received by the receiver unit and amplified by the corresponding amplifier unit. The echo data stored is applied to the digital adder memory 8 in synchronism with the delay pulse from the delay timing pulse generator 4 and is added to the echo data from the other amplifier units in the digital adder memory 8.

FIG. 14 shows a detailed arrangement of the digital adder memory 8. The output signals from the A/D converter units in the A/D converter 6 are input to the input terminals of an adder 81. The output terminal of the adder 81 is connected to a memory 82. The data stored in the memory 82 is input to the envelope detector 9. A clock signal from the A/D converter 6 is input to one of the input terminals of an OR gate 83. A signal from the envelope detector 9 is applied to the other input terminal of the OR gate 83. The output signal from the OR gate 83 is input to an address counter 84. The count of the address counter 84 is input as an address signal to the memory 82. An END signal from the address counter 84 is input to the signal control circuit 18 and a reset signal from the signal control circuit 18 to the address counter 84. The adder memory thus arranged adds together the echo signals received by the transducer units into one wave data which in turn is stored in the memory 82. The wave data stored is then input to the envelope detector 9 where it is envelope-detected.

Figure 15:
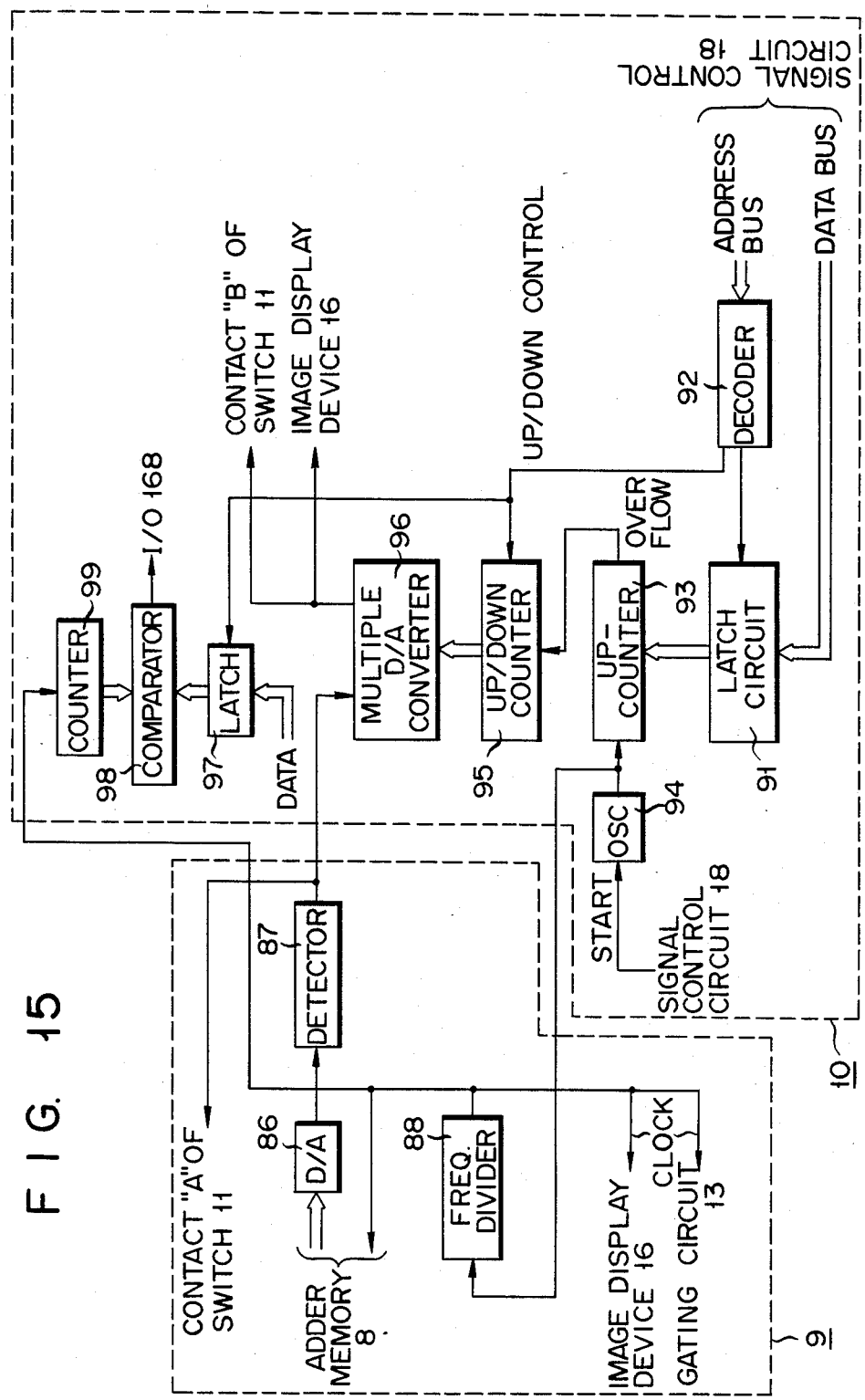
FIG. 15 shows a block diagram of an envelope detector and a correcting circuit, which are assembled into the non-destructive testing apparatus shown in FIG. 1.

FIG. 15 shows a detailed arrangement of the envelope detector 9 and the correcting circuit 10.

An D/A converter 86 converts the data from the digital adder memory 8 into an analog signal. The analog signal is then transferred to a detector circuit 87. The envelope-detected signal is applied to the correcting circuit 10. An output signal from the correcting circuit 10 is applied to a frequency divider 88. The first output signal from the frequency divider 88 is input to the OR gate 83 of the digital adder memory 8. A second output signal as a clock signal is applied to the gating circuit 13 of the A-scope display 12 and also to the image display device 16. The first and second output signals are synchronized with each other.

Correction data is input from the RAM 17 through the data bus to a latch circuit 91. An address signal is applied from the RAM 17 through the address bus to a decoder 92. The output decoded by the decoder 92 is input as a latch signal to the latch circuit 91. The correction data latched is then input as a preset signal to an up-counter 93. The up-counter 93 is supplied with a block signal from an oscillator 94. The up-counter 93 counts the clock signal from the up-counter 93 till its count reaches the preset value. The oscillator 94 starts to operate in response to a start signal from the signal control circuit 18. The up-counter 93, when its count exceeds the preset value, produces an overflow signal. The overflow signal is input to an up/down counter 95. The up/down counter 95 receives a control signal to designate an up-count mode or a down count mode, which is produced from the decoder 92. The count of the up/down counter 95 is input to a D/A converter 96. While receiving the signal from the envelope detector 9, a D/A converter 96 multiplies the count from the up/down counter 95 by the output signal of the envelope detector 9. The result of the multiplication is produced from the correcting circuit 10, as its output signal. The data from the RAM 17 is latched in the latch circuit 97 which receives a latch signal from the decoder 92. The data read out from the latch circuit 97 is then input to a comparator 98. An output signal of the frequency divider 88 in the envelope detector 9 is input to a counter 99 which then counts the signal input. The output of the counter 99 is input to the comparator 98 where it is compared with the data from the latch circuit 97. The result of the comparison is input to the signal control circuit 18.

The envelope detector 9 produces an overflow signal every time it counts the number of clock pulses corresponding to the correction data latched in the latch circuit 91. Accordingly, in an up count mode, the up/down counter 95 is incremented by one every time the up-counter 93 produces an overflow signal. In other words, the contents of the up/down counter 95 increases linearly. Since the D/A converter 96 multiplies the linearly increasing contents of the up/down counter 95 by the echo wave signal derived from the up/down counter 95. Accordingly, the output signal from the D/A converter 96 gradually and linearly increases. The decoder 92 sets the up/down counter 95 in an up count mode or a down count mode according to each correction data input to the latch circuit 91. Each address signal input to the decoder 92 contains a flag bit to indicate whether the present data is greater or less than the next data. The flag bit is "1" when the former is greater than the latter, and is "0" in the reverse case. And when the flag bit is "1", the up/down counter 95 is set in an up count mode. The same is set in a down count mode when the flag is "0". In an up count mode, the output of the up/down counter 95 linearly increases, as described above. Then, the next correction value is read out and when it is less than the preceding one, the up/down counter 95 is set in a down count mode. As a result, the output of the up/down counter 95 linearly decreases. In this way, the linear correction is performed.

FIG. 16 shows a detailed arrangement of the gating circuit 13 in the A-scope display 12. A gate circuit 101 receives the output signal from the image display device 16 as a control signal and controls the transfer of the output signal from the correcting circuit 10 to the gating circuit 13. The gate circuit 102 receives the output signal from the image display device 16 as a gate control signal and controls the fetching operation of the output signal from the envelope detector 9. The output signal from the image display device 16 is input as a gate control signal to the gate circuit 103, thereby to control the fetching of the clock signal from the oscillator 105. The output signal from the envelope detector 9 and the clock signal from the gate circuit 103 fetched by the gate circuit 103 are input to an OR gate 106 of which the output is input as a counter clock pulse to the wave memory 14. The output signal from the image display device 16 is input to a one-shot MM 107. The output signal from the one-shot MM 107 is input as a reset pulse to the wave memory 14.

The wave memory 14 will be described referring to FIG. 17.

The output signal fetched from the correcting circuit 10 by the gate circuit 101 in the gating circuit 13 is input to an A/D converter 111 where it is converted into a digital signal. A signal fetched through the gate circuits 102 and 103 is applied to an address counter 113 in the wave memory 14 where it is counted. The count of the address counter 113 is applied as an address signal to the memory 112. The output signal from the one-shot MM 107 in the gating circuit 13 is input as a reset pulse to the memory 112 and the address counter 113. The data stored in the memory 112 is converted into an analog signal which serves as a signal $Y_A$ indicating a position on the Y axis of the A-scope image. The count of the address counter 113 is input to a D/A converter 115 where it is converted into an analog signal. The analog signal serves as a signal indicating a position $X_A$ on an X axis of the A-scope image to be intensity-displayed, a signal indicating a position $X_D$ on the X-axis of the discriminating level display signal, and a position $X_G$ on the X axis indicating a gate range. The output signal from the one-shot MM 107 in the gating circuit 13 is also input to a one-shot MM 116 in the wave memory 14. The output signal from the one-shot MM 116 serves as an intensity display indicating signal $Z_A$ in the A-scope image. First to fourth decoders 117 to 120 are supplied with signals for indicating a minimum value of the gate range, a maximum of the gate range, a discriminating level and an intensity display from a digital display ($G_1$), a digital panel ($G_2$), a digital panel (discriminate), and a digital panel (brightness). The decoded output from the decoders 117 to 120 are respectively applied to comparators 121 to 124. These comparators 121, 122 and 124 respectively compare the decoded outputs with the count of the address counter 113. The comparator 123 compares data stored in the memory 112 with the decoded output from the decoder 119. The output of the comparator 121 is directly input to one of the input terminals of an AND gate 125. The output of the comparator 122 is connected to the other input terminal of the AND gate 125 via an inverter 126. The output signal from the AND gate 125 is transferred as an intensity display indicating signal $Z_G$ for a gate range to the wave memory 14 of the A-scope display 12. V+ is used as a signal for indicating a position $Y_G$ on an Y axis in the gate range. The output signal of the AND gate 125 is input as a gate control signal to gate circuits 127 and 128. The gate circuit 127 controls the transfer of the memory output from the memory 112 under control of the output signal from the AND gate 125. The comparator 123 applies its output signal to the gate circuit 128. The gate circuit 128 controls the transfer of the data from the comparator 123 control of the output signal from the AND gate 125. The output signal from the comparator 124 is input to a one-shot MM 129. The one-shot MM 129 is input as an intensity display indicating signal $Z_D$ to the wave memory 14 of the A-scope display 12.

The output signal of the decoder 119 is also input to a D/A converter 130 and is input as a signal representative of a position on the Y axis of the discriminating level to the wave memory 14 in the A-scope display 12. The signal fetched by the gate circuits 127 and 128 is input to a latch circuit 131 and a comparator 132. The comparator 132 compares the output signal of the latch circuit 131 with the signals from the gate circuits 127 and 128. The output signal from the comparator 132 is applied as a latch signal to the latch circuit 131. The latch signal is produced when the signal from the gate circuits 127 and 128 is smaller than the output signal from the latch circuit 131. The data from the latch circuit 131 is stored in a RAM 133 and input to the signal control circuit 18. The data stored in the RAM 133 is converted into an analog signal by a D/A converter 134 and the converted signal is applied as a signal indicating a maximum echo signal to the display 15. The signal applied to the gate circuit 128 is input as a latch signal to a latch circuit 135. The count output from the address counter 113 is input to the latch circuit 135 and is latched in the latch circuit 135 by the latch signal from a gate circuit 128. The data latched in the latch circuit 135 is stored into the ROM 135 and input to the signal control circuit 18. The data stored in the ROM 135 is read out to a D/A converter 137 and is converted into an analog signal which is input to the display 15 as a signal representing a position where the A-scope image is in excess of a discriminating level.

Figure 18:
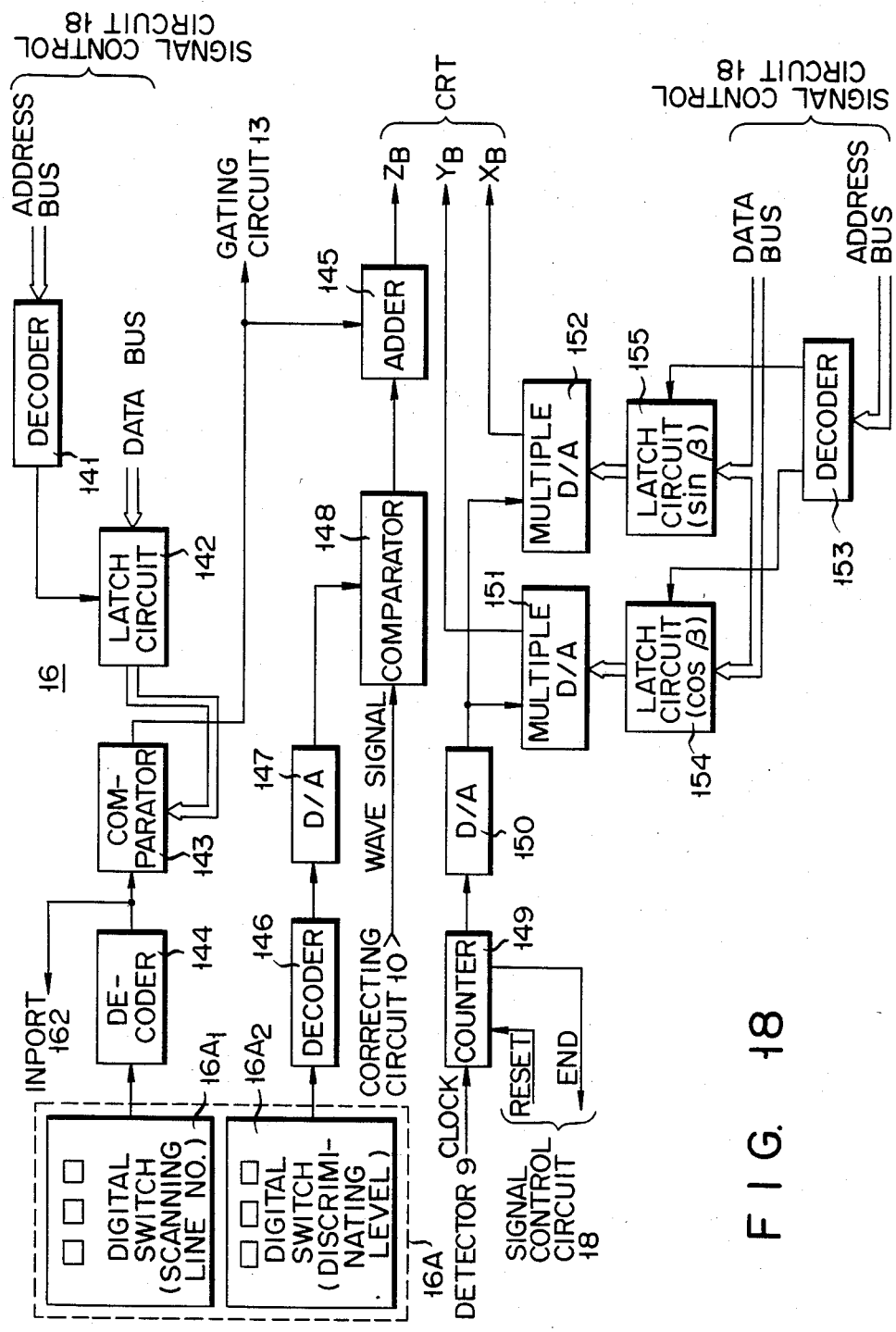
FIG. 18 is a block diagram of an image display device used in the non-destructive testing apparatus of FIG. 1.

FIG. 18 shows a detailed arrangement of the image display device 16.

An address signal is input from the signal control circuit 18 over an address bus to a decoder 141. The data from the decoder 141 is input as the latch signal to the latch circuit 142. To a latch circuit 142, the data on the scanning line is applied as the data to be latched, over the data bus. The output signal from the latch circuit 142 is input to a comparator 143.

A signal indicating a scanning line number is input from a decoder 144 and decoded therein. The decoded signal is applied to the comparator 143 where it is compared with the signal from the latch circuit 142. The output signal from the comparator 143 is input to the gating circuit 13 of the A-scope display 12 and input to an decoder 144. A signal representing a discriminating level is input from the digital panel to a decoder 146 where it is decoded. The decoded signal is input to a D/A converter 147 where it is converted into an analog signal. The analog signal converted is then input to a comparator 148. The echo wave signal is input from the correcting circuit 10 to the comparator 148 which compares the wave signal with the discriminating level analog signal from the D/A converter 147. The result of the comparison is applied to the adder 145. The adder 145 adds together the output signals from the comparator 148 and the comparator 143, and produces the result of the addition as a signal $Z_B$ for an intensity display indication of the B-scope image.

A clock signal from the envelope detector 9 is applied to a counter 149. The signal control circuit 18 applies a reset signal to the counter 149, while the counter 149 applies an end signal to the signal control circuit 18. The count of the counter 149 is input to a D/A converter 150 where it is converted into an analog signal. The analog signal is input to multiplier D/A converters 151 and 152. An address signal is input from the signal control circuit 18 to a decoder 153 over the address bus. The decoder 153 decodes the address signal. The decoded signal is input as a latch signal to latch circuits 154 and 155. The signal control circuit 18 applies the data of cos $\beta$ and sin $\beta$ as data to be latched to the latch circuits 154 and 155, through the data bus. $\beta$ is an angle defined between the ultrasonic beam and Y-axis of two-dimensional coordinate. The signals latched by the latch circuits 154 and 155 are input to multiplier D/A converters 151 and 152, respectively. The multiplier D/A converter 151 multiplies the analog signal from the D/A converter 150 by the output signal cos $\beta$ from the latch circuit 154, and produces a signal $Y_B$ representing a position on the Y axis on the B-scope image. The multiplier D/A converter 152 multiplies the analog signal from the D/A converter 150 by the output signal sine $\beta$ from the latch circuit 155 and produces its output signal as a signal $X_B$ representing a position on the X axis on the B-scope image.

Figure 19:
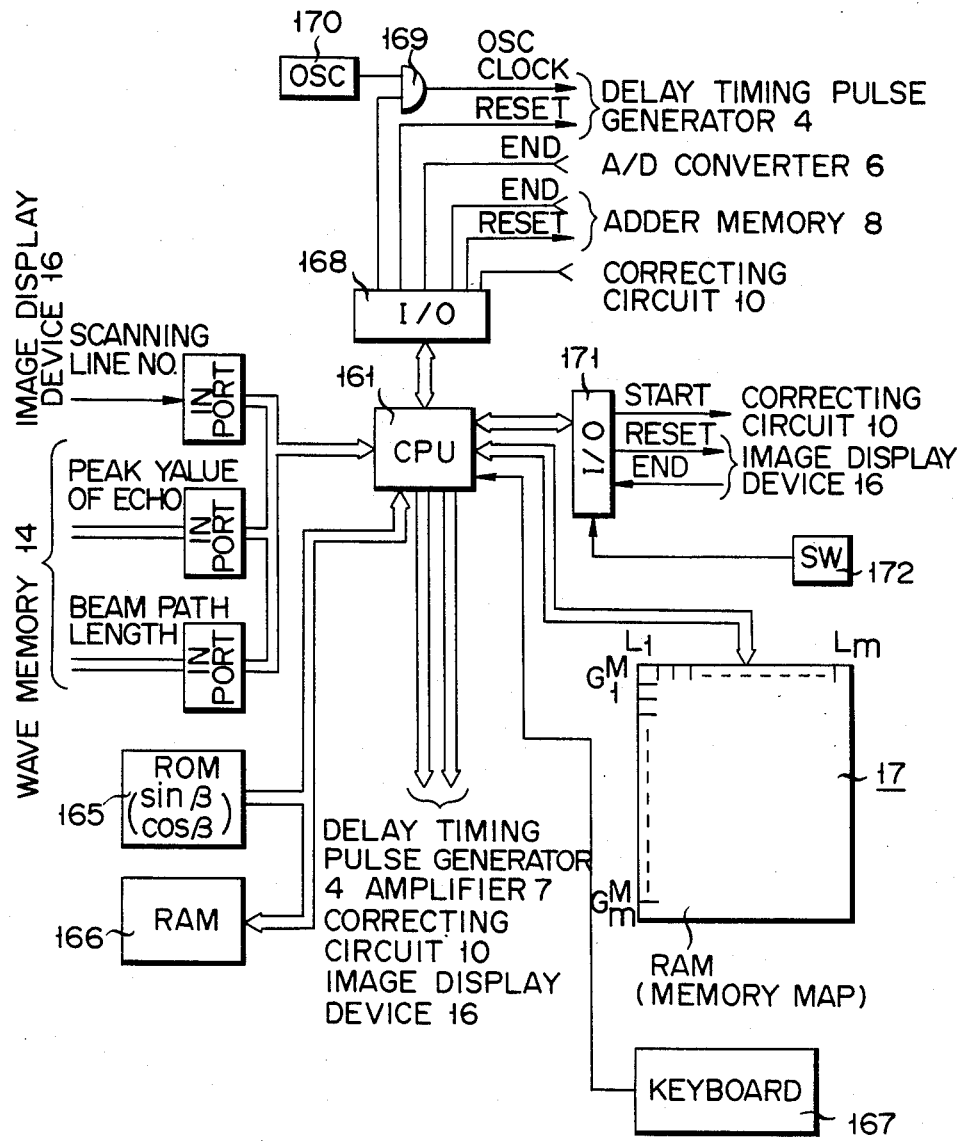
FIG. 19 is a block diagram of a signal control circuit 18 used in the non-destructive testing apparatus of FIG. 1.

FIG. 19 shows a detailed arrangement of the signal control circuit 18.

The number of scanning lines, a maximum crest value, and a position on the beam propagating path are input through INPORTs 162, 163 and 164 to a central processing unit (CPU) 161. The CPU 161 is coupled with a read only memory (ROM) 165 for storing the data sine $\beta$ and cos $\beta$ and a random access memory (RAM) 166 for storing the data. A key board 167 coupled with the CPU 161 is for entering various types of commands to the CPU 161. The CPU 161 is connected to a memory map 17 as a RAM, which stores the corection values and the like. An end signal is applied from the digital adder memory 8 to the CPU 161 through the I/O device 168. The CPU 161 applies a reset signal to the digital adder memory 8 through the I/O device 168. The A/D converter 6 applies an end signal to the CPU 161 via the I/O device 168. The CPU 161 applies a reset signal to the signal control circuit 18 via the I/O device 168. The CPU 161 further produces a signal for transmission to one of the input terminals of an AND gate 169 for controlling the same gate. A clock signal is input from an oscillator 170 to the other input terminal of the AND gate 169. When opened by the gate control signal from the CPU 161, the AND gate 169 allows the clock signal from the oscillator 170 to pass therethrough to the delay timing pulse generator 4. The CPU 161 applies a start signal to the correcting circuit 10 via an I/O device 171. The same outputs a reset signal to the image display device 16 by way of the I/O device 171 and receives the end signal through the I/O device 171. A switch circuit SW 172 connected to the I/O device 171 is operated to set the I/O device 171 in an operating state. Between the CPU 161 and the delay timing pulse generator 4, the amplifier 7, the correcting circuit 10, the wave memory 14 and the image display device 16, the data transfer is performed through the data bus and the address signal transfer is done through the address bus. It should be understood that this invention is not limited to the above-mentioned embodiment. An alternative display method for displaying the gate set range to the display 15 and the wave signal discriminating level increases or decreases an intensity of the displayed waveform 26 by the gate setting range, or increases or decreases an intensity at a point where the waveform signal crosses the waveform signal discriminating level.

In the above embodiment, the amplifier units and the D/A converter units are formed as a pair and corresponding to the ultrasonic pulse receiver units. Alternatively, a single channel selector is provided at the postsage of the ultrasonic pulse receiver 3. By the number of the ultrasonic pulse receiver units selected by the channel selector, the amplifier units are connected to the D/A converter units. Also in this arrangement, the necessary number of the ultrasonic pulse receiver units are sequentially selected, and the received echo signals are applied to the digital adder memory 6, thereby to obtain a single delay added waveform signal. In the sector scanning, to effect a symmetrical scanning, the correction value of only the left or the right half of the scanning range is obtained. The correction value obtained is used commonly for both the halves of the scanning range. In this case, the memory 17 is sufficient to have the memory capacity capable of storing the scanning lines of the half scanning range, not the entire scanning range.

According to the embodiment as mentioned above, during the course of defect finding, the correction value can be modified by switching a plurality of the memory maps provided additionally. If necessary, the DAC curve can be displayed on the display 15 by multiplying the reciprocal of the correction value by a predetermined value. This idea can easily be implemented using a proper known circuit.

In focusing the ultrasonic beams in the electronic scanning, the ultrasonic waves distance attenuation characteristic differs with a change of the focal distance. To cope with this problem, a plurality of memory maps are prepared. The correction values for correcting the distance attenuation characteristic corresponding to the focal distances are stored in the memory maps. In the correction, the necessary data is read out from the memory maps.

The A/D converter 6, which delays and adds the ultrasonic waves from the resonators in the digital form, may be replaced by a delay/addition system using usual analog delay lines or CCD. This invention is applicable for the non-destructive testing apparatus using additionally a magnetic tape or a magnetic disc, or by mechanically vibrating an array type probe.

Further, this invention is applicable for the non-destructive testing apparatus using a called aperture-composing method based on the electronic scanning. In this case, the defect finding accuracy is improved since the defect finding sensitivity is corrected when the ultrasonic waves are transmitted and received while the object is scanned at a wide angle with the ultrasonic waves.

Figure 20A:
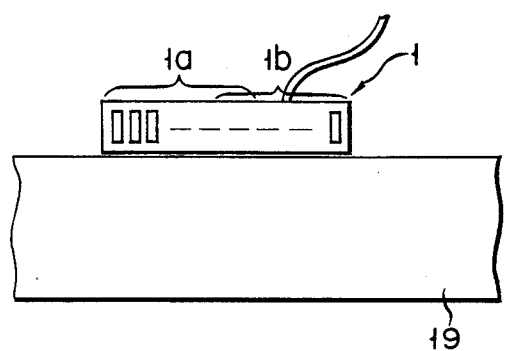
FIG. 20A illustrates a probe placed on the body under defect inspection, the probe being different from that of FIG. 2A.
Figure 20B:
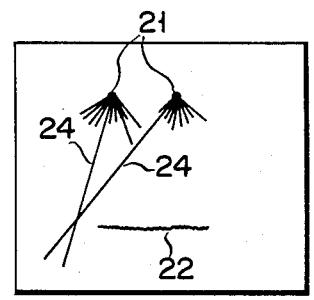
FIG. 20B shows a B-scope waveform received by the probe of FIG. 20A and displayed on the screen of the image display device.
Figure 21A:
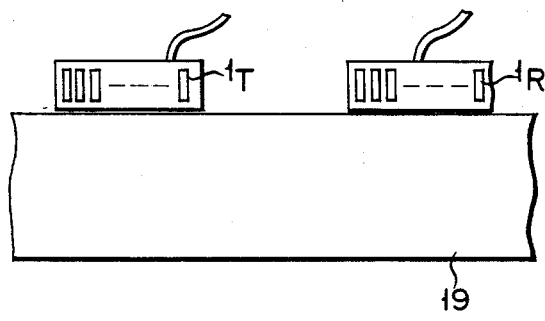
FIG. 21A shows yet another probe placed on the body under defect inspection.
Figure 21B:
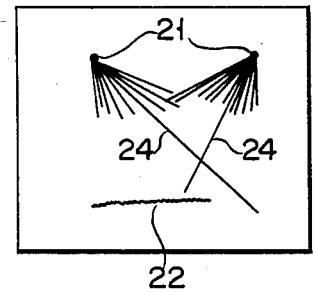
FIG. 21B shows a B-scope waveform received by the probe of FIG. 21A and displayed on the screen of the image display device.

The resonators may be provided separately for the transmission and the reception. This will be described in detail. As shown in FIG. 20A, the transducers 1a of the probe 1 are for transmission, while the transducers 1b are for reception. Alternatively, separate probes 1$_T$ and 1$_R$ are provided for the transmission and reception, respectively, as shown in FIG. 21A. The transmitting transducers 1a and the receiving transducers 1b, which is illustrated overlapped, may be provided separately. FIGS. 20B and 21B respectively are B-scope images when the echo is transmitted and received using the probes shown in FIGS. 20A and 21A. The above-mentioned embodiment employs the signal discriminating levels individually set up for the image display device 16 and the A-scope display 12. The discriminating level for the image display device 16 may be set following that for the A-scope display 12. This approach can provide a more exact signal waveform of the defect, which is displayed on the image display device.

As described above, according to this invention, in detecting the defect by the electronic scanning method, the ultrasonic beam incident direction is used for setting the range for setting the segment for defect detecting and for setting the waveform signal discriminating level for detecting a level of the waveform signal. Because of this feature, an exact display of the ultrasonic received signal waveform is ensured. Further, the distance amplitude attenuation in the course of the propagating of the ultrasonic waves is corrected for displaying the tomogram of the structural member. Therefore, the display accuracy of the defect is remarkably improved, and the result of the defect detection can be checked for a short time using both the waveform of the received ultrasonic wave and the image displayed.

What is claimed is:

1. An ultrasonic non-destructive testing apparatus of the electronic scanning type comprising:

transmitter means for producing exciting pulses in response to a predetermined timing pulse;

a probe coupled to said transmitter means, having a plurality of transducers for transmitting ultrasonic waves, in a calibration mode, into a calibrating member having known defective portions and for receiving the echoes from the known defective portions, and in a test mode, into a body to be tested and for receiving the echoes from unknown defective portions of the body;

signal processing means coupled to said probe for processing said echoes received by said probe to generate an echo signal;

means for obtaining reference correcting data for correcting amplitude attenuations of echoes from the known defective portions of said calibrating member and also for obtaining interpolating data for interpolating the reference correcting data in a beam propagation direction and a scan direction;

means coupled to said signal processing means for correcting amplitude attenuations of the echoes from the unknown defective portions of the body by using said reference correcting data and interpolating data; and display means coupled to said correcting means for displaying a wave with regard to said body on the basis of the corrected echo signal.

2. An ultrasonic non-destructive testing apparatus according to claim 1, wherein said interpolating data is obtained by using memory means coupled to said signal processing means for storing the reference correcting data and means coupled to said memory means for calculating said interpolating data on the basis of said reference correcting data stored in said memory means.

3. An ultrasonic non-destructive testing apparatus according to claim 1, further comprising A-scope display means coupled to one selected from said signal processing means and said correcting means, for displaying an A-scope image of the echo signal of said selected means and displaying a predetermined sampling range to the echo signal of said selected means.

4. An ultrasonic non-destructive testing apparatus according to claim 3, wherein said A-scope display means displays a maximum level of strength of the echo signal received within said sampling range.

5. An ultrasonic non-destructive testing apparatus according to claim 1, further comprising A-scope display means coupled to one selected from said signal processing means and said correcting means, for displaying an A-scope image of the echo signal of said selected means and displaying a predetermined level of strength to the echo signal of said selected means.

6. An ultrasonic non-destructive testing apparatus according to claim 4, wherein said A-scope display means displays a location on the echo signal where said echo signal exceeds said predetermined level.

7. An ultrasonic non-destructive testing apparatus according to claim 1, further comprising A-scope display means coupled to one selected from said signal processing means and said correcting means, for displaying an A-scope image of the echo signal of said selected means, displaying a predetermined sampling range to the echo signal from said selected means, and displaying a predetermined level to the echo signal of said selected means.

8. An ultrasonic non-destructive testing apparatus according to claim 1, further comprising A-scope display means coupled to one selected from said signal processing means and said correcting means, for displaying an A-scope image of the echo signal of said selected means and displaying a maximum level of strength of the echo signal of said selected means received within a predetermined sampling range.

9. An ultrasonic non-destructive testing apparatus according to claim 1, further comprising A-scope display means coupled to one selected from said signal processing means and said correcting means, for displaying an A-scope image of the echo signal of said selected means and displaying a location on the echo signal of said selected means where the echo signal exceeds a predetermined level of strength.

10. An ultrasonic non-destructive testing apparatus according to claim 1, further comprising A-scope display means coupled to one selected from said signal processing means and said correcting means, displaying a maximum level of strength of the echo signal of said selected means received within a predetermined sampling range, and displaying a location on the echo signal of said selected means where the echo signal exceeds a predetermined level of strength.

11. An ultrasonic non-destructive testing apparatus according to claim 1, further comprising A-scope display means coupled to one selected from said signal processing means and said correcting means, for displaying an A-scope image of the echo signal of said selected means, displaying a predetermined sampling range to the echo signal of said selected means, displaying a predetermined level of strength to the echo signal, displaying a maximum level of strength of the echo signal received within a predetermined sampling range, and displaying a location on the echo signal where the echo signal exceeds a predetermined level of strength.

12. An ultrasonic non-destructive testing apparatus according to claim 1, wherein said correcting means functions in two arithmetic manners, one being multiplication of an amplitude of the echo signal from said signal processing means by said reference and interpolating data and the other being division of an amplitude of the echo signal from said signal processing means by said reference and interpolating data.

13. An ultrasonic non-destructive testing apparatus according to claim 12, wherein said correcting means has a multiple digital to analog converter.

14. An ultrasonic non-destructive testing apparatus according to claim 1, wherein said displaying means displays a B-scope image of said body.

* * * * *